United States Patent
Ferrino et al.

(10) Patent No.: US 8,049,021 B2
(45) Date of Patent: Nov. 1, 2011

(54) PROCESS FOR THE PREPARATION OF FLUOROTETRAENE

(75) Inventors: Sergio Ferrino, Yautepec (MX); Diego Torres, Cuernavaca (MX); Vilas Dahanukar, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 860 days.

(21) Appl. No.: 12/052,852

(22) Filed: Mar. 21, 2008

(65) Prior Publication Data

US 2008/0234506 A1     Sep. 25, 2008

Related U.S. Application Data

(60) Provisional application No. 61/012,533, filed on Dec. 10, 2007.

(30) Foreign Application Priority Data

Mar. 23, 2007 (IN) .............................. 596/CHE/2007

(51) Int. Cl.
C07J 5/00 (2006.01)
(52) U.S. Cl. ...................................................... 552/557
(58) Field of Classification Search .................. 552/557
See application file for complete search history.

(56) References Cited

U.S. PATENT DOCUMENTS 3,210,341 A    10/1965    Lincoln et al.
4,524,134 A     6/1985    Kominek et al.

FOREIGN PATENT DOCUMENTS

WO     03/082896 A2    10/2003

OTHER PUBLICATIONS

J.S. Mills, A. Bowers, C. Djerassi and H.J. Ringold, J. Am. Chem. Soc. 82, 3399 (1960).

*Primary Examiner* — Barbara P Badio
(74) *Attorney, Agent, or Firm* — Thomas C. McKenzie; Balaram Gupta; Robert A. Franks

(57) ABSTRACT

There is provided a process for preparing 21-acetyloxy-6-alpha-fluoro-pregna-1,4,9(11),16-tetraene-3,20-dione compound of Formula I, which comprises reacting 21-acetyloxy-pregna-1,3,5,9(11),16-pentaene-3-oxo acetate with a fluorinating agent.

19 Claims, No Drawings

PROCESS FOR THE PREPARATION OF FLUOROTETRAENE

TECHNICAL FIELD

The present application relates to a process for the preparation of fluorotetraene, which is a useful intermediate in the synthesis of several corticosteroids, including flunisolide hemihydrate, fluocinolone acetonide, fluocinonide, flumethasone and other fluoro-corticoids.

BACKGROUND

Fluorotetraene is chemically described as 21-acetyloxy-6-alpha-fluoro-pregna-1,4,9(11),16-tetraene-3,20-dione (hereinafter referred as "fluorotetraene") and can be represented by the structural Formula I.

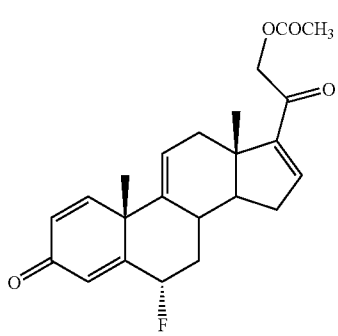

Formula I

Corticosteroids are a class of steroid hormones that are produced in the adrenal cortex. Corticosteroids are involved in a wide range of physiological processes such as stress response, immune response and regulation of inflammation, carbohydrate metabolism, protein catabolism, blood electrolyte levels, and behavior.

U.S. Pat. No. 3,210,341 describe 6α-fluoro steroids, process for their preparation and their use in treatment of various inflammatory conditions.

U.S. Pat. No. 4,524,134 describe preparation of 1,2-dehydro steroids from their corresponding 1,2-staturated derivatives.

International Application Publication No. WO 03/082896 A2 describe preparation of several 6α-fluoro steroids and their pharmaceutically acceptable salts.

It would be a contribution to the art to provide a process for the preparation of fluorotetraene compound of the Formula I, which is used as an intermediate for synthesis of several corticosteroids.

SUMMARY

The present application relates to a process for the preparation of fluorotetraene, which is useful as an intermediate for the synthesis of corticosteroids such as flunisolide hemihydrate, fluocinolone acetonide, fluocinonide, flumethasone and other fluoro-corticoids.

In one aspect, the present application provides a process for the preparation of fluorotetraene of Formula I, which process includes:

a) reacting 21-acetyloxy-pregna-1,4,9(11),16-tetraene-3,20-dione acetate compound of Formula III with an acetylating agent to afford 21-acetyloxy-pregna-1,3,5,9(11),16-pentaene-3-oxo, acetate compound of Formula II; and

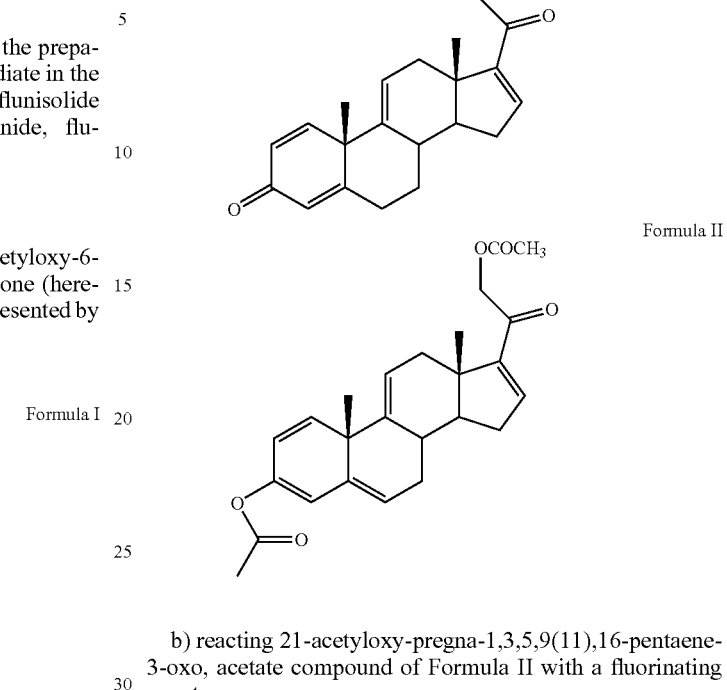

b) reacting 21-acetyloxy-pregna-1,3,5,9(11),16-pentaene-3-oxo, acetate compound of Formula II with a fluorinating agent.

In another aspect, the present application provides 21-acetyloxy-pregna-1,3,5,9(11),16-pentaene-3-oxo, acetate compound of Formula II.

In yet another aspect, the present application relates to use of compound of Formula II and fluorotetraene of the present application in the synthesis of corticosteroids.

DETAILED DESCRIPTION

The present application relates to a process for the preparation of fluorotetraene, which is useful as an intermediate for the synthesis of corticosteroids such as flunisolide hemihydrate, fluocinolone acetonide, fluocinonide, flumethasone and other fluoro-corticoids.

In one aspect, the present application provides a process for the preparation of fluorotetraene of Formula I which process includes:

a) reacting 21-acetyloxy-pregna-1,4,9(11),16-tetraene-3,20-dione acetate compound of Formula III with an acetylating agent to afford 21-acetyloxy-pregna-1,3,5,9(11),16-pentaene-3-oxo, acetate compound of Formula II; and

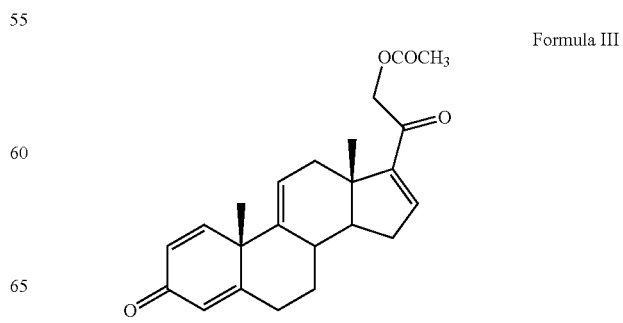

Formula III

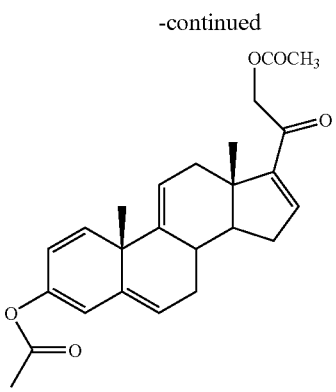

Formula II b) reacting 21-acetyloxy-pregna-1,3,5,9(11),16-pentaene-3-oxo, acetate compound of Formula II with a fluorinating agent.

Suitable acetylating agents which can be used in step (a) include, but are not limited to, acetic anhydride, acetyl chloride, and isopropenyl acetate.

The acetylation reaction can be carried out in the presence of a catalyst such as an acid or its salt with a base for example p-toluene sulphonic acid, PPTS (pyridine p-toluene sulphonic acid salt).

The acetylation reaction may be carried out in the presence of an inert solvent. Suitable inert solvents which may be used include halogenated solvents such as dichloromethane, ethylene dichloride and chloroform; hydrocarbon solvents such as toluene, xylene, n-hexane, n-heptane and cyclohexane; esters such as ethyl acetate, isopropyl acetate and tertiary-butyl acetate; nitriles such as acetonitrile, propionitrile and butyronitrile; aprotic polar solvents such as dimethylsulfoxide (DMSO), N,N-dimethylformamide (DMF), dimethylacetamide (DMAC), and N-methylpyrrolidinone (NMP); and mixtures thereof in various proportions without limitation.

The acetylation reaction can also be carried out without an external solvent wherein the acetylating agent act both as reagent and solvent.

Suitable temperatures for conducting the reaction can range from about −25° C. to about 100° C., preferably from about 70° C. to about 90° C. The reaction can be conducted till the completion of the reaction. Typically the reaction time varies from about 30 minutes to about 10 hours.

The molar ratio of compound of Formula III to the acetylating agent can range from about 1:1 to about 1:5.

After completion of the reaction, the organic layer containing the product is separated and can be proceeded to next step directly or it can be processed to isolate pure compound of Formula II.

Step b) involves reacting 21-acetyloxy-pregna-1,3,5,9(11),16-pentaene-3-oxo, acetate compound of Formula II with a fluorinating agent.

Suitable fluorinating agents which can be used in step (b) include, but are not limited to, N-fluoro N-chloromethyl triethylene diamine bis tetrafluoroborate (product marketed by Air Products and Chemicals, Inc. under the trade name SELECTFLUOR™), 1-fluoro-4-hydroxy-1,4-diazadicyclo [2.2.2.] octane-di-tetrafluoroborate (product marketed by AlliedSignal Corp. under the trade name ACCUFLUOR™), 1-fluoro-benzensulphonamide, perchloryl fluoride and mixtures thereof.

Any solvent in which the fluorinating agent is soluble can be used as the reaction solvent. Suitable organic solvents that can be used include, but are not limited to: alcohols such as methanol, ethanol, n-propanol, isopropyl alcohol, n-butanol and tertiary-butyl alcohol; ketones such as acetone, methyl ethyl ketone and methyl isobutyl ketone; halogenated solvents such as dichloromethane, dichloroethane and chloroform; hydrocarbon solvents such as toluene, xylene and cyclohexane; esters such as ethyl acetate, isopropyl acetate and tertiary-butyl acetate; nitriles such as acetonitrile, propionitrile; aprotic polar solvents such as DMSO, DMF, DMAC and NMP; or their combinations in various proportions without limitation.

Suitable temperatures for conducting the reaction can range from about −25° C. to about 50° C., preferably from about −10° C. to about 25° C. The reaction can be conducted until the completion of the reaction. Typically reaction time varies from about 30 minutes to about 5 hours.

After completion of the reaction organic layer containing the product is separated and may be proceeded to next step directly or it can be concentrated to form a residue. The residue thus obtained can optionally be further purified by crystallizing from a suitable solvent. Suitable solvents that can be used in the purification process include but are not limited to: ketonic solvents such as acetone, ethyl methyl ketone and methyl isobutyl ketone; esters such as ethyl acetate, n-propyl acetate, n-butyl acetate and tertiary-butyl acetate; and nitrile solvents such as acetonitrile and propionitrile, hydrocarbons such as n-hexane, cyclohexane, tolune, xylene and the like.

The wet cake obtained above optionally may be further dried with or without vacuum. Drying can be suitably carried out in a tray dryer, vacuum oven, air oven, fluidized bed drier, spin flash dryer and flash dryer. Drying can be carried out at temperatures of about 35° C. to about 70° C. Drying can be carried out for any desired time periods such as from about 1 to 20 hours, or longer.

The process of the present application yields substantially pure fluorotetraene of Formula I. The purity of fluorotetraene realized by the process of the present application can be further enriched by effecting one or more, for example two or three, slurrying or recrystallisation procedures.

Fluorotetraene of Formula I has a purity of at least about 95% by weight, preferably 98% by weight, more preferably 99% by weight. More particularly 6β-isomer impurity content is not more than 2% by weight; preferably not more than 1% by weight, more preferably is not more than 0.5% by weight as determined by using high performance liquid chromatography (HPLC).

The fluorotetraene compound of Formula I thus obtained by the above process can be further converted to the corticosteroid compounds such as flunisolide hemihydrate, fluocinolone acetonide, fluocinonide, flumethasone and other fluorocorticoids by following procedures known in the art such as U.S. Pat. No. 3,210,341, which is incorporated herein by reference in its entirety and for the purpose stated, and J. S. Mills, A. Bowers, C. Djerassi and H. J. Ringold, *J. Am. Chem. Soc.* 82, 3399 (1960).

In another aspect, the present application provides an intermediate compound of Formula II useful in the synthesis of the compound of Formula I which is characterized by spectral analysis techniques, including $^1$H NMR, infrared absorption spectroscopy, and mass spectrometry.

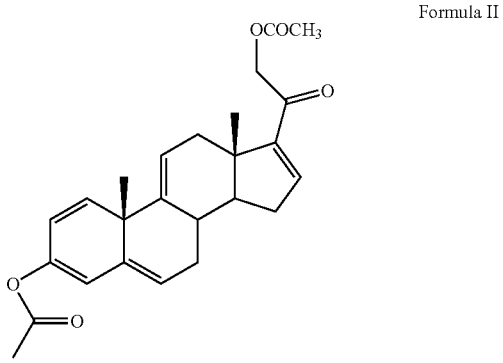

Formula II

In yet another aspect the present application is related to use of the compound of Formula II and fluorotetraene of the present application in the synthesis of corticosteroids.

Having described the invention, other embodiments will become apparent to one skilled in the art from consideration of the specification. The invention is further explained by reference to the following examples describing certain specific aspects and embodiments of the invention. It will be apparent to those skilled in the art that many modifications, both to materials and methods, may be practiced without departing from the scope of the invention, and such modifications are encompassed by the invention.

EXAMPLES

Example 1

PREPARATION OF 21-ACETYLOXY-PREGNA-1,3,5,9(11),16-PENTAENE-3-OXO ACETATE (FORMULA II)

15 g of 21-acetyloxy-pregna-1,4,9(11),16-tetraene-3,20-dione acetate of Formula III, 73.6 ml of isopropenyl acetate and 1.5 g of para-toluene sulfonic acid monohydrate were charged into a clean and dry 4 neck round bottom flask under a nitrogen atmosphere, followed by heating to about 80° C. The resultant reaction mixture was stirred at about 80° C. for about 4 hours. After completion of the reaction, the reaction solution was cooled to about 27° C. followed adjusting the pH to about 8 by the addition of 2.9 ml of triethylamine. The resultant solution was distilled completely at about 55° C. to afford 17 g of the title compound.

Example 2

PREPARATION OF 21-ACETYLOXY-6-ALPHA-FLUORO-PREGNA-1,4,9(11),16-TETRAENE-3,20-DIONE (FORMULA I)

15.6 g of N-fluoro N-chloromethyl triethylen diamine bis tetrafluoroborate (trade name Selectfluor) and 294 ml of acetonitrile were charged into a clean and dry 4 neck round bottom flask under a nitrogen atmosphere, followed by cooling to about −10° C. 15 g of tetraene enol acetate of Formula II dissolved in 147 ml of acetonitrile under a nitrogen atmosphere was added at about −10° C. over about 60 minutes. The reaction was allowed to reach a temperature of about 25° C. followed by stirring for about 4 hours. After completion of the reaction, the reaction was quenched by the addition of 294 ml of water. The decomposed reaction suspension was extracted with 2×225 ml of dichloromethane followed by washing the organic layer with 225 ml of 5% aqueous sodium bicarbonate solution. Organic and aqueous phases were separated and the organic phase was washed with 2×205 ml of water. Organic and aqueous phases were separated and the aqueous phase was extracted with 2×112 ml of dichloromethane. Total organic layer was dried over anhydrous sodium sulphate followed by distillation of solvent completely at about 45° C. The residue was mixed with hexane, 50 ml and mixed with silica gel (15 g) loaded into chromatography column and eluted with a mixture of hexane and ethyl acetate in the ratio of 65:35. The fractions were collected and distilled at about 45° C. to a volume of about 45 ml on the total volume. The resultant residual solution was cooled to about −5° C. followed by stirring for about 30 minutes. Separated solid was filtered and the solid washed with hexane followed by drying the solid at about 50° C. under vacuum over about 24 hours to afford 11.6 g of the title compound.

Assay by HPLC: 99.1% by weight.
Melting Range: 193-194° C.

The invention claimed is:

1. A process for preparing 21-acetyloxy-6-alpha-fluoro-pregna-1,4,9(11),16-tetraene-3,20-dione compound of Formula I, which comprises reacting 21-acetyloxy-pregna-1,3,5,9(11),16-pentaene-3-oxo acetate compound of Formula II with a fluorinating agent

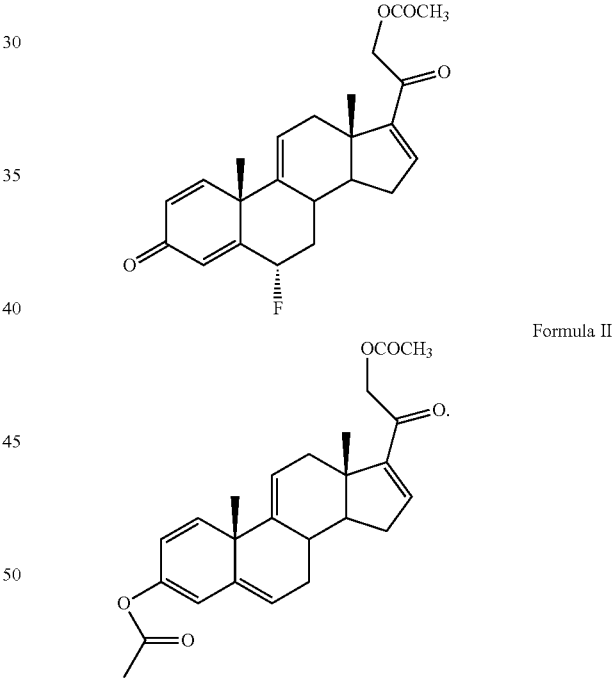

2. The process of claim 1, wherein the fluorinating agent is selected from the group consisting of N-fluoro-N-chloromethyltriethylenediamine bis tetrafluoroborate, 1-fluoro-4-hydroxy-1,4-diazadicyclo[2.2.2]octane di tetrafluoroborate, 1-fluoro-benzensulphonamide, and perchloryl fluoride.

3. The process of claim 1, wherein the fluorinating agent is N-fluoro-N-chloromethyltriethylenediamine bis tetrafluoroborate.

4. The process of claim 1, wherein the reaction is carried out in a polar aprotic solvent.

5. The process of claim 1, wherein the reaction is carried out in a solvent selected from the group consisting of acetone, methyl ethyl ketone, methyl isobutyl ketone, THF, acetonitrile, propionitrile, butyronitrile, dimethylsulfoxide (DMSO), N,N-dimethylformamide (DMF), dimethylacetamide (DMAC), and N-methylpyrrolidinone (NMP).

6. The process of claim 5, wherein the reaction is carried out in acetonitrile.

7. The process of claim 1, where in the reaction temperature ranges from about −25° C. to about +50° C.

8. The process of claim 6, wherein the reaction temperature ranges from about −25° C. to about +50° C.

9. The process of claim 1, where in the compound of Formula I has purity of about 95% or more by weight.

10. The process of claim 1, where in the compound of Formula I has purity of about 98% or more by weight.

11. The process of claim 1, where in the compound of Formula I has purity of about 99% or more by weight.

12. A compound of the Formula II

Formula II

13. A process for the preparation of 21-acetyloxy-pregna-1,3,5,9(11),16-pentaene-3-oxo acetate compound of Formula II, which comprises reaction of 21-acetyloxy-pregna-1,4,9(11),16-tetraene-3,20-dione acetate compound of the Formula III with an acetylating agent

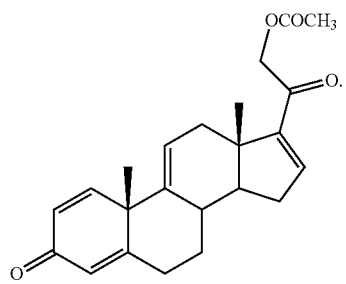

Formula III

14. The process of claim 13, wherein the acetylating agent is selected from the group consisting of isopropenyl acetate, acetic anhydride, and acetyl chloride.

15. The process of claim 13, wherein the acetylating agent is isopropenyl acetate.

16. The process of claim 13, wherein the reaction is carried out in the presence of a catalyst, which is p-toluene sulphonic acid or pyridine p-toluene sulphonic acid salt.

17. The process of claim 13, wherein the reaction is carried out in the absence of solvent.

18. The process of claim 13, wherein the reaction temperature ranges from about −25° C. to about +100° C.

19. A process for the preparation of 21-acetyloxy-6-alpha-fluoro-pregna-1,4,9(11),16-tetraene-3,20-dione compound of Formula I, which process comprises:

a) reacting 21-acetyloxy-pregna-1,4,9(11),16-tetraene-3,20-dione acetate compound of Formula III with an acetylating agent to obtain 21-acetyloxy-pregna-1,3,5,9(11),16-pentaene-3-oxo acetate compound of the Formula II; and b) reacting 21-acetyloxy-pregna-1,3,5,9(11),16-pentaene-3-oxo acetate compound of the Formula II with a fluorinating agent.

* * * * *